United States Patent
Pourmand et al.

(10) Patent No.: US 7,501,253 B2
(45) Date of Patent: Mar. 10, 2009

(54) DNA FINGERPRINTING USING A BRANCH MIGRATION ASSAY

(75) Inventors: Nader Pourmand, San Mateo, CA (US); Ronald W. Davis, Palo Alto, CA (US); Shan X. Wang, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/789,559

(22) Filed: Apr. 24, 2007

(65) Prior Publication Data

US 2007/0287156 A1    Dec. 13, 2007

Related U.S. Application Data

(63) Continuation-in-part of application No. 11/231,657, filed on Sep. 20, 2005, now Pat. No. 7,238,486.

(60) Provisional application No. 60/612,000, filed on Sep. 21, 2004.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ...................... 435/6; 536/23.1, 24.3
See application file for complete search history.

(56) References Cited

U.S. PATENT DOCUMENTS

| | | | |
|---|---|---|---|
| 4,725,537 A | 2/1988 | Fritsch et al. | |
| 5,753,439 A | 5/1998 | Smith et al. | |
| 6,150,095 A | 11/2000 | Southern et al. | |
| 6,238,927 B1 | 5/2001 | Abrams et al. | |
| 6,261,784 B1 | 7/2001 | Nadeau et al. | |
| 6,379,888 B1 | 4/2002 | Nadeau et al. | |
| 6,579,680 B2 | 6/2003 | Frutos et al. | |
| 6,815,164 B2 | 11/2004 | Krun | |
| 7,238,486 B2 * | 7/2007 | Pourmand et al. | 435/6 |
| 2004/0235114 A1 | 11/2004 | Yang et al. | |

OTHER PUBLICATIONS

R. Radtkey et al., Rapid, high fidelity analysis of simple sequence repeats on an electronically active DNA chip. Nucleic Acids Research, 28:E17 (2000).*

* cited by examiner

*Primary Examiner*—Ethan Whisenant
(74) *Attorney, Agent, or Firm*—Lumen Patent Firm

(57) ABSTRACT

A method of determining the length of a polynucleotide target is provided. With this method, a target is first hybridized to an array of first probes having different, determined lengths, resulting in the formation of duplexes between the polynucleotide target and the first probes. These duplexes have a single stranded section of target if the target is longer than the first probe it is in a duplex with, and a single stranded section of probe if the target is shorter than the first probe it is in a duplex with. Next, a series of probes is hybridized to the duplexes, breaking apart duplexes in which the target and probe have unequal lengths through the process of branch migration. Thus, the target only remains bound in the duplex if the target and probe are of equal lengths. The length of the polynucleotide target can thereby be determined.

15 Claims, 6 Drawing Sheets

(2 of 6 Drawing Sheet(s) Filed in Color)

FIG. 1
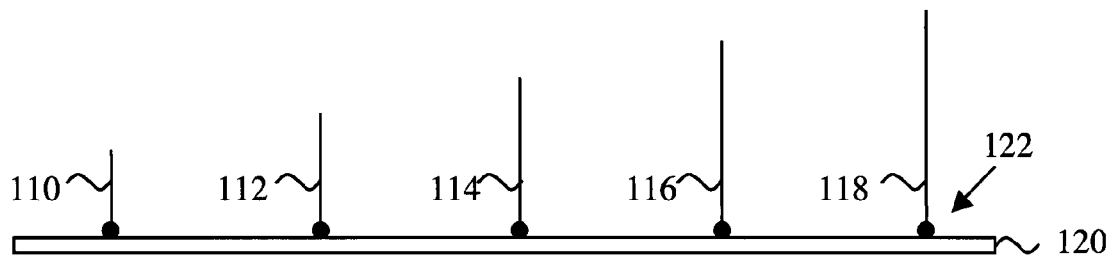
A
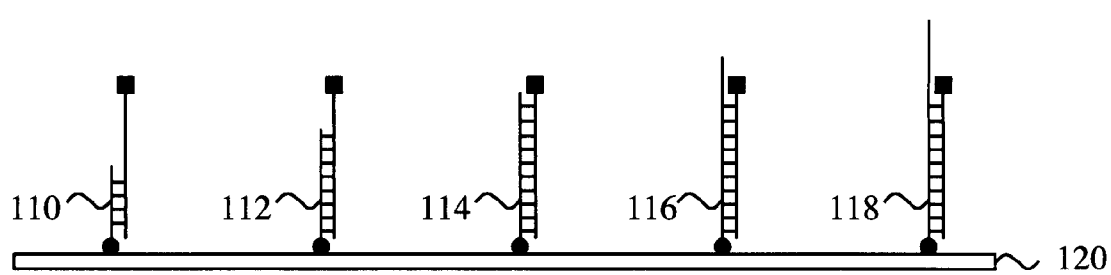
B
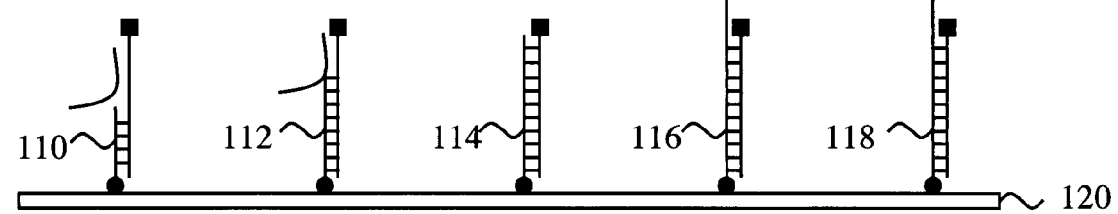
C
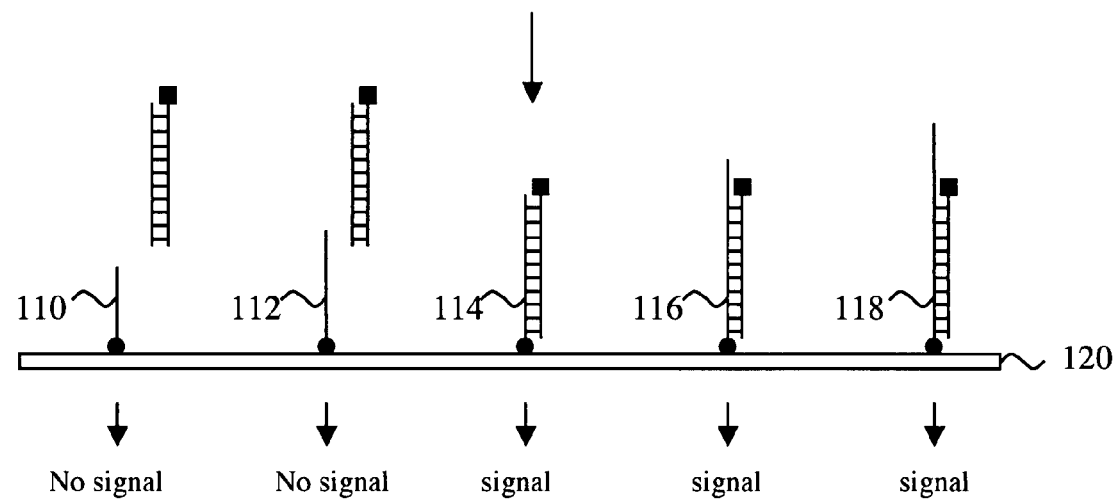
D

FIG. 2-A
A
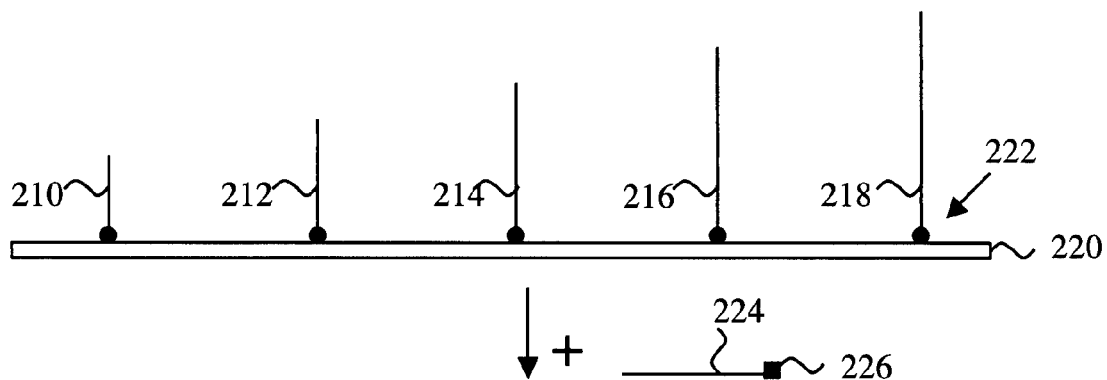
B
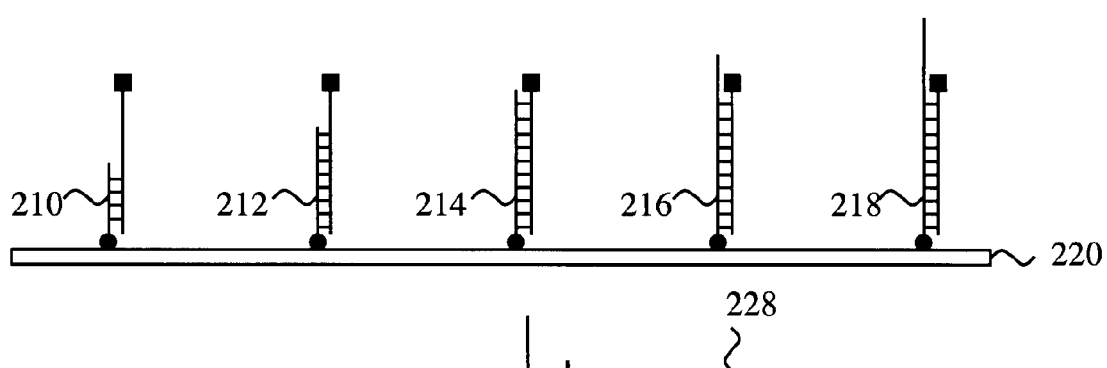
C
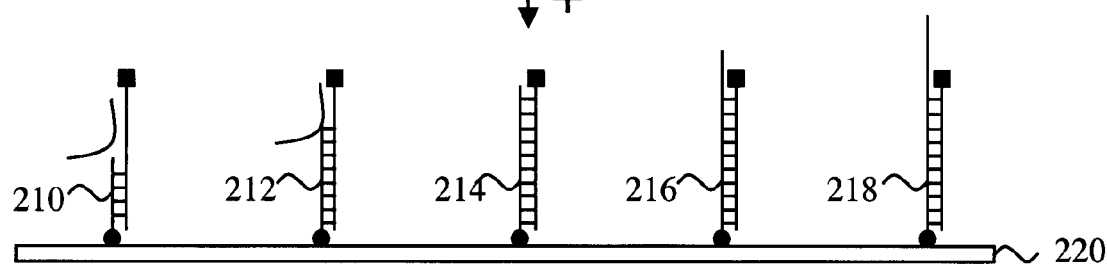
D
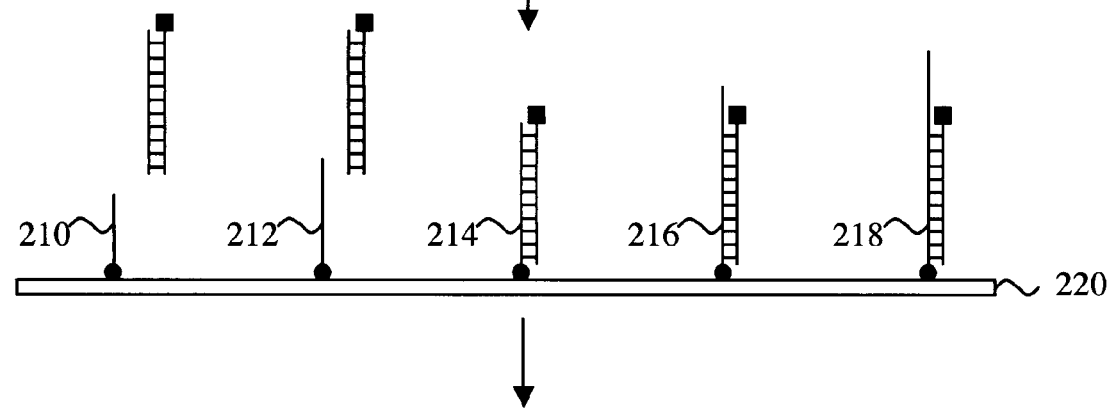

FIG. 2-B
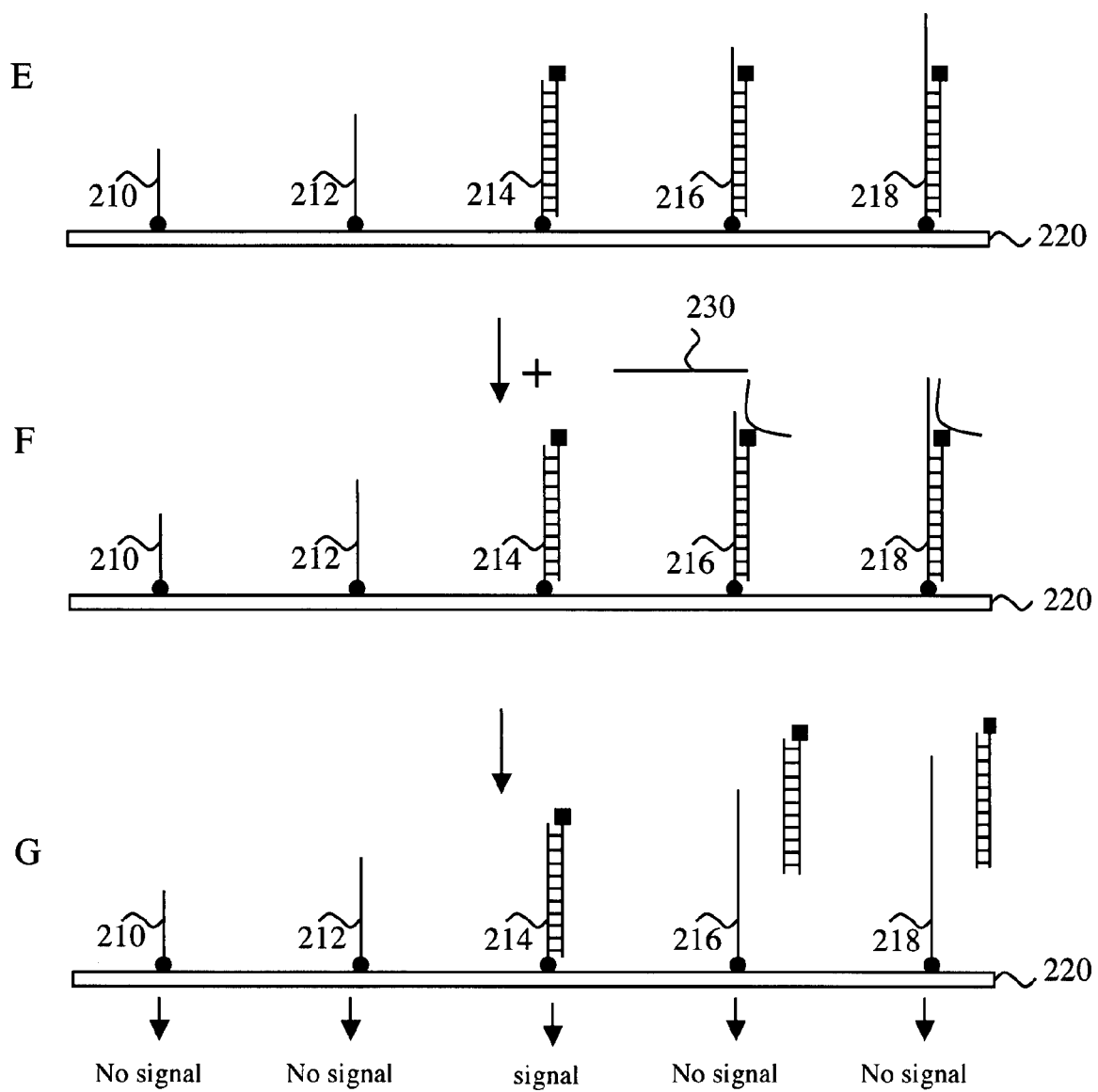

SEQUENCE LISTING

```
<160> NUMBER OF SEQ ID NOS: 14

<210> SEQ ID NO 1
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 1
ttctgagcca cttggactga gagcgtttat ttgcccaaac att            43

<210> SEQ ID NO 2
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 2
ttctgagcca cttggactga gctgttctaa gtacttccta tct            43

<210> SEQ ID NO 3
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 3
ttctgagcca cttggactga gttatacctc tatctaccta tct            43

<210> SEQ ID NO 4
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
```

```
<222> LOCATION: (1)..(1)
<223> OTHER INFORMATION: amino-linker (5AmMC6)

<400> SEQUENCE: 4
ttctgagcca cttggactga gaaaaactat caatctgtct atc            43

<210> SEQ ID NO 5
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 5
ttctgagcca cttggactga gaaagataga tagatgattg ata            43

<210> SEQ ID NO 6
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 6
ttctgagcca cttggactga gtgttttgtc tttcaatgat atc            43

<210> SEQ ID NO 7
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 7
ttctgagcca cttggactga gccctctctt tttcttactt tct            43

<210> SEQ ID NO 8
<211> LENGTH: 20
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)
<220> FEATURE:
<221> NAME/KEY: misc_feature
<222> LOCATION: (20)..(20)
<223> OTHER INFORMATION: Biotin

<400> SEQUENCE: 8
tttttttttt tttttttttt                                      20

<210> SEQ ID NO 9
<211> LENGTH: 20
<212> TYPE: DNA
```

```
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)
<220> FEATURE:
<221> NAME/KEY: misc_feature
<222> LOCATION: (20)..(20)
<223> OTHER INFORMATION: Cy3

<400> SEQUENCE: 9
tctgagccac ttggactgag                                              20

<210> SEQ ID NO 10
<211> LENGTH: 20
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: amino-linker (5AmMC6)

<400> SEQUENCE: 10
tttttttttt tttttttttt                                              20

<210> SEQ ID NO 11
<211> LENGTH: 31
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: Biotin

<400> SEQUENCE: 11
cttgtcatag tttaggaacg aactaacgat a                                 31

<210> SEQ ID NO 12
<211> LENGTH: 35
<212> TYPE: DNA
<213> ORGANISM: Artificial
<220> FEATURE:
<223> OTHER INFORMATION: oligonucleotide

<400> SEQUENCE: 12
tatttagtga gataaaaaaa aactatcaat ctgtc                             35

<210> SEQ ID NO 13
<211> LENGTH: 30
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..()
<223> OTHER INFORMATION: Biotin

<400> SEQUENCE: 13
gatcaataca gacagacaga caggtggata                                   30

<210> SEQ ID NO 14
<211> LENGTH: 36
```

```
-continued

<212> TYPE: DNA
<213> ORGANISM: Artificial
<220> FEATURE:
<223> OTHER INFORMATION: oligonucleotide

<400> SEQUENCE: 14
tatctatcat ccatctcttg ttttgtcttt caatga                                   36
```

DNA FINGERPRINTING USING A BRANCH MIGRATION ASSAY

CROSS-REFERENCE TO RELATED APPLICATIONS

This application is a continuation-in-part of U.S. patent application Ser. No. 11/231,657, filed Sep. 20, 2005 now U.S. Pat. No. 7,238,486, which claims priority from U.S. Provisional Application No. 60/612,000, filed Sep. 21, 2004, both of which are incorporated herein by reference.

STATEMENT REGARDING FEDERALLY SPONSORED RESEARCH OR DEVELOPMENT

This invention was made in part with government support under grant no. NOOO14-02-0807 awarded by the U.S. Defense Advanced Research Projects Agency. The government has certain rights in this invention.

FIELD OF THE INVENTION

The present invention relates generally to DNA fingerprinting. More particularly, the present invention relates to a method of determining the length of a polynucleotide target using a branch migration assay.

BACKGROUND

DNA fingerprinting (also known as DNA profiling) using short tandem repeats (STRs) has become the method of choice for human identification in forensic sciences, finding applications in different circumstances such as determination of perpetrators of violent crime, resolving unestablished paternity, and identifying remains of missing persons or victims of mass disaster. STRs are highly polymorphic microsatellite regions of 2-7 bp localized in noncoding regions of DNA. Every individual has a different pattern of STRs due to a different number of repeats and micro-variation in the sequences of the repeats.

The FBI and the forensic science community typically use 13 separate STR loci (the core CODIS loci) in routine forensic analysis. (CODIS refers to the Combined DNA Index System that was established by the FBI in 1998). If two DNA samples have identical lengths at all 13 loci, the probability that the two samples did not originate from the same individual is approximately one to ten billion. The courts generally accept this identification as definitive evidence that the individuals in question are the same. It is believed that STR analysis will remain the technique of choice in forensic science for DNA fingerprinting for the next decade, and that the number of loci used in this analysis will perhaps increase from 13 to 20.

Generally, to perform a DNA fingerprinting experiment based on STR analysis, the regions of DNA corresponding to each of the 13 STR loci are excised from sample DNA using appropriate restriction enzymes. The regions are then amplified using PCR and labeled with a dye or fluorescent molecule. The length of the DNA molecules is then determined using polyacrylamide gel electrophoresis (PAGE) or other known electrophoretic separation techniques, see, e.g., John M. Butler "Forensic DNA Typing" Academic Press, 2001.

Electrophoresis is a separation technique based on size, i.e., shorter DNA molecules migrate more rapidly down a gel or capillary than longer DNA molecules. The population of molecules (in this case, STR regions) is thus separated by size (or repeat length), and the final position of the DNA is determined by visualizing the staining pattern of the dye or fluorescent molecule. While there are miniature systems with an array of electrophoretic columns for this measurement, the number of STR regions and samples that can be identified using these miniature systems is relatively small.

Although still in their infancy, several DNA fingerprinting methods using microarrays have been proposed. For example, R. Radtkey et al., in "Rapid, high fidelity analysis of simple sequence repeats on an electronically active DNA chip" *Nucleic Acids Research*, 28:E17 (2000), offer a high stringency approach for discriminating STR alleles based on active microarray hybridization. A sandwich hybrid is assembled, in which proper base stacking of juxtaposed terminal nucleotides results in a thermodynamically favored complex. The increased stability of this complex relative to non-stacked termini and/or base pair mismatches is used to determine the identification of STR alleles. While this method has the advantage of being able to test many samples and STRs in a small instrument, it has the disadvantage of requiring the use of a special electronically active DNA array to allow discrimination of subtle hybridization differences between repeats of similar lengths. Thus, this method has not been widely adopted.

Another proposed microarray method involves the use of ligase and/or polymerase to detect the length of a VNTR (variable number of tandem repeats). For example. U.S. Pat. No. 6,150,095 discloses a technique in which the length of a VNTR is detected by hybridizing a target to a short probe to form a duplex, incubating the duplex with labeled nucleotides, and monitoring chain extension of the probe as an indication of the length of the variable number repeat section of the target. Other methods to determine the length of VNTR involve the use of ligation of tags combined with base extension. VNTR-based DNA fingerprinting has largely been superseded by STR-based DNA fingerprinting.

U.S. Pat. No. 5,753,439 discloses a method of using nuclease to nick mismatched base pairs followed by nick translation using DNA polymerase. With this method, target DNA is labeled and hybridized to a differently labeled probe. Mismatched bases due to differences in the length of the repeat region between the probe and the target are nicked with nuclease, and the remainder of the probe or target is elongated using nick translation, thereby displacing the label on the target or probe. This method is complicated and thus has not gained wide adoption.

Accordingly, there is a need in the art to develop new, simple DNA fingerprinting methods utilizing widely available microarrays for rapid determination of individual identity.

SUMMARY OF THE INVENTION

The present invention provides methods of determining the length of a polynucleotide target that take advantage of the process of branch migration. Branch migration is a process by which a single invading single-stranded polynucleotide extends its partial pairing with its complimentary strand as it displaces the resident strand from a polynucleotide duplex. In one embodiment, a polynucleotide target is first hybridized to an array of first probes having different, determined lengths, resulting in the formation of duplexes between the polynucleotide target and the first probes. These duplexes have a single stranded section of target polynucleotide if the target polynucleotide is longer than the first probe it is in a duplex with. Next, a second probe having a determined length is hybridized to these duplexes. Preferably, the second probe is similar in sequence to the sequence of one of the immobilized probes.

More preferably, is identical in sequence to one of the first probes. Alternatively, the second probe may be an array of probes that are identical to the array of first probes. If the length of the target polynucleotide is greater than the length of the first probe, and thus has a single stranded section, it is displaced during this hybridization step by the process of branch migration. In contrast, if the length of the target polynucleotide is less than or equal to the length of the first probe, it is not displaced. Thus, the length of the target polynucleotide can be determined by identifying in which duplexes the target polynucleotide was displaced.

In alternative embodiment, the method includes an additional step. In this step, a third probe having a determined length is hybridized to the duplexes. Preferably, the second probe is complementary to the sequence of one of the first probes. More preferably, the second probe is complementary to the sequence of the longest of the first probes. With this step, the third probe displaces the target polynucleotide from the duplex if the target polynucleotide is shorter than the length of the first probe, meaning the duplex has a single-stranded section of probe. At the end of this step, the target only remains if it is equal in length to the length of the first probe. Therefore, the length of the target polynucleotide can be determined by identifying in which of the duplexes the target polynucleotide was not displaced.

The target polynucleotide and first, second, and third probes may be any nucleic acid or nucleic acid analog, preferably single or double-stranded DNA. In the case of double-stranded DNA, the DNA is denatured prior to hybridization, e.g. by heating to 95° C. Preferably, the target polynucleotide and first, second and third probes have repeated nucleotide sequences, with the number of repeated sequences in the target polynucleotide and first, second and third probes determining the lengths of the target polynucleotide and first, second, and third probes. The repeated sequences may be of any length, but are preferably between about 2 to about 7 base pairs long. Examples of repeated sequences identifiable by this invention include short tandem repeats (STRs) and tri-nucleotide repeats. In a preferred embodiment, the first, second, and third probes also have a non-repeated nucleotide sequence that is complimentary to a non-repeated nucleotide sequence in the target.

In a preferred embodiment, only the target polynucleotide is labeled. Alternatively, the target polynucleotide, first, second or third probes may be labeled with distinct labels, respectively. Any label may be used, including but not limited to fluorescent particles, magnetic nanoparticles, and biotin.

Preferably, the array of first probes is attached to a solid support. More preferably, the first probes are attached to predetermined positions on the solid support to form a microarray. The array of first probes may be attached by any means, including but not limited to chemical linkage, biological linkage, sulfur linkage of probes modified with a sulfur containing group, and amino-linkage of probes modified with an amine group.

In another embodiment, the invention provides a method of automatically determining repeat length based on data obtained using the inventive methods.

BRIEF DESCRIPTION OF THE FIGURES

The patent or application file contains at least one drawing executed in color. Copies of this patent or patent application publication with color drawing(s) will be provided by the Office upon request and payment of the necessary fee.

The present invention together with its objectives and advantages will be understood by reading the following description in conjunction with the drawings, in which:

FIG. 1 shows an example of an embodiment of a branch migration assay according to the present invention.

FIG. 2 shows an example of another embodiment of a branch migration assay according to the present invention.

DETAILED DESCRIPTION OF THE INVENTION

Figure 3:
FIG. 3 shows an example of results from the embodiment of the branch migration assay shown in FIG. 1.

The present invention provides methods of determining the length of a polynucleotide target using a branch migration assay, an example of which is shown in FIG. 1. In this example, an array of single-stranded polynucleotide first probes 110, 112, 114, 116, 118, having one, two, three, four, and five repeats, respectively, are attached to the surface of microarray 120 through attachment domain 122 (FIG. 1A). In a first step, a single-stranded target polynucleotide 124 labeled with label 126 and having three repeats is hybridized to the first probes (FIG. 1B). Target polynucleotide 124 hybridizes with first probes 110 and 112 to form a duplex with a single-stranded region of target polynucleotide 124. The duplex formed by target polynucleotide 124 and first probe 114 has no single-stranded regions. The duplex formed by target polynucleotide 124 and first probes 116 and 118 has single-stranded regions of first probe.

Next, an unlabeled single-stranded polynucleotide second probe 128, which is complimentary to target polynucleotide 124, is hybridized with the duplexes (FIG. 1C). Branch migration is more thermodynamically favorable in the presence of single-stranded polynucleotide. Thus, second probe 128 displaces target polynucleotide 124 only from the duplexes in which there is a single stranded region of target polynucleotide 124 present, i.e. the duplexes containing probes 110 and 112 (FIG. 1D). Displacement of target polynucleotide 124 from probes 110 and 112 can be detected by a loss of signal due to displacement of label 126 from these duplexes. By identifying which duplexes have had target polynucleotide 124 displaced, the length, and hence the number of repeats, in target polynucleotide 124 can be determined. In this case, since signal is lost from duplexes containing first probes 110 and 112, having one and two repeats, respectively, target polynucleotide 124 is determined to have three repeats.

In another example, shown in FIG. 2, an array of single-stranded polynucleotide first probes 210, 212, 214, 216, 218, having one, two, three, four, and five repeats, respectively, are attached to the surface of microarray 220 through attachment domain 222 (FIG. 2A). In a first step, a single-stranded target polynucleotide 224 labeled with label 126 and having three repeats is hybridized to the first probes (FIG. 2B). Target polynucleotide 224 hybridizes with first probes 210 and 212 to form a duplex with a single-stranded region of target polynucleotide 224. The duplex formed by target polynucleotide 224 and first probe 214 has no single-stranded regions. The duplex formed by target polynucleotide 224 and first probes 216 and 218 has single-stranded regions of first probe.

Next, an unlabeled single-stranded polynucleotide second probe 228, which is complimentary to target polynucleotide 224, is hybridized with the duplexes (FIG. 2C). Preferably, second probe 228 is complementary to the longest hypothetical target polynucleotide. Branch migration is more thermodynamically favorable in the presence of single-stranded polynucleotide. Thus, second probe 228 displaces target polynucleotide 224 only from the duplexes in which there is a single stranded region of target polynucleotide 224 present, i.e. the duplexes containing probes 210 and 212 (FIGS. 2D, E).

In the next step, an unlabeled single-stranded polynucleotide third probe 230, which is complimentary to one of the first probes, is hybridized with the duplexes (FIG. 2F). Preferably, third probe 230 is complimentary to the longest of the first probes, i.e. probe 218. As branch migration is more thermodynamically favorable in the presence of single-stranded polynucleotide, third probe 230 displaces target polynucleotide 224 from the duplexes in which there is a single stranded region of first probe present, i.e. duplexes containing probes 216 and 218. (FIG. 2G). Thus, signal only remains if the target is the same length as the probe (FIG. 2G).

A key requirement for this assay is that the target polynucleotide hybridizes to the first probes in the proper register. That is, it must hybridize without misaligned repeats or "slippage". For example, in FIG. 1B, it must be ensured that polynucleotide target 124 binds probes 116 and 118 starting at the repeat on the first probe that is closest to the microarray surface. Otherwise, the polynucleotide target could hybridize to first probes 116 and 118 such that there is a single stranded region of polynucleotide target in addition to a single-stranded region of probe in the duplex. This would result in displacement of the polynucleotide target from probes 116 and 118 by second probe 128, loss of signal 126 from probes 116 and 118, and misidentification of the number of repeats in polynucleotide target 124. Therefore, in a preferred embodiment, the first, second, and third probes contain a non-repeated nucleotide sequence that is complementary to a non-repeated sequence on the polynucleotide target. For example, if the first probe is attached to the surface of the microarray at the 5' end, there would be a non-repeated sequence 5' to the repeated sequences in the first probe, which is complimentary to the target polynucleotide. The same sequence would be present in the 5' end of the second probe.

The branch migration assay may be carried out with any detection system, for instance, a standard fluorescence technology. In addition to conventional fluorescence microarrays, the assay could also be carried out using high-sensitivity magnetic detector arrays such as spin-valve arrays and magnetic tunneling junction arrays.

In another embodiment, the invention provides a method of automating analysis of data obtained using the above methods to determine repeat length of the target, as well as heterozygosity or homozygosity of the sample from which the target was obtained. To automate the microarray analysis and extraction of repeat length from raw data, a multilayer artificial neural network (ANN) was designed and software was developed to analyze raw array fluorescence data and extract the specific number of repeats in a test target sequence. The main task of the ANN software is to differentiate between homozygous samples with one fluorescence peak and heterozygous samples with two peaks. This problem is particularly challenging for heterozygotes that differ very little in repeat length. These two overlapping patterns are difficult to classify by a simple set of algebraic or logistic rules, but the use of neural network heuristics helped to overcome this difficulty. For this purpose, other heuristic-based methods could be used, for example, on Statistical Learning Theory, such as Support Vector Machines (SVM). However, the training and optimization tools provided with available neural network packages were convincing factors to use it in final processing. We developed ANN software utilizing BrainMaker Professional 3.52 software (California Scientific Software, Berkeley, Calif.). The neural network contains two main components: 1) an ANN module with customized feed forward run-time code, including a STR trained network, and 2) a mathematical rule-based algorithm to find peak location corresponding to repeat length.

The input to the ANN software was the fluorescence intensities associated with each feature on the array. These intensities were processed by a trained network of connections with learned weights and converted by a transfer function to specified output values. Output values, in this case, were statistical weight sums identifying homozygous or heterozygous samples. The larger the output sum for either type, the higher the accuracy in identification of the sample type. Output values were scaled by ANN design as decimal values from 0 to 1. These were considered as likelihood values of ANN recognition for identifying homozygous or heterozygous samples (where the sum of their output values is close to 1).

Extensive training and testing of the STR neural network was performed with BrainMaker software. To train the network, data was used from 65 STR microarrays containing targets of known repeat type and length. Each run consisted of 22 measured mean fluorescence intensities from spots corresponding to different numbers of probe repeats and can be thus represented by a histogram of 22 values. Seven STR microarrays were then used as "blind" runs for testing the ANN. To maximize the difficulty for ANN pattern recognition, the test cases included some of the most challenging potential scenarios. These included several homozygous samples with similar numbers of repeats, as well as heterozygous samples containing two repeats similar in length. Even in these difficult cases, the calls from the inventive ANN software were identical to the known STR repeat lengths in all cases, including homozygotes and heterozygotes.

EXAMPLES

Methods

First Probe Preparation

The first probes were prepared by oligonucleotide synthesis. Probes were synthesized for detection of 7 STR loci (TPOX, CSF1PO, D5S818, D7S820, D13S317, D16S539, D18S51) each having from 1 to 22 repeats. These STR loci are the simplest ones, with just 4 nucleotides repeated and no variation in sequence. The first probes were synthesized with an amino-modification at the 5' end that allows the oligo to bind to the chip surface, followed by a common sequence, a unique sequence (a genomic sequence located 3' of the repeats, which is specific for each STR locus) and nucleotide repeats (from 1 to 22), so that for each STR locus there were 22 probes. The unique sequence and the repeats were both complementary to the genomic sequence of the target. Table 1 shows the sequences of the first probes (SEQ ID NO: 1-7), with the amino modification shown between slashes, the common sequence shown in plain text, the unique sequence underlined, and the repeat sequence in bold. Only one repeat is shown for each STR probe in Table 1.

TABLE 1

| STR name | SEQ ID NO: | SEQUENCE |
|---|---|---|
| TPOX | 1 | 5'-/5AmMC6/TTCTGAGCCACTTGGACTGAG<u>AGCGTTTATTTGCCCAAA</u>CATT |
| CSF1PO | 2 | 5'-/5AmMC6/TTCTGAGCCACTTGGACTGAG<u>CTGTTCTAAGTACTTCCT</u>ATCT |
| D5S818 | 3 | 5'-/5AmMC6/TTCTGAGCCACTTGGACTGAG<u>TTATACCTCTATCTACCT</u>ATCT |
| D7S820 | 4 | 5'-/5AmMC6/TTCTGAGCCACTTGGACTGAG<u>AAAAACTATCAATCTGTC</u>TATC |
| D13S317 | 5 | 5'-/5AmMC6/TTCTGAGCCACTTGGACTGAG<u>AAAGATAGATAGATGATT</u>GATA |
| D16S539 | 6 | 5'-/5AmMC6/TTCTGAGCCACTTGGACTGAG<u>TGTTTTGTCTTTCAATGA</u>TATC |
| D18S51 | 7 | 5'-/5AmMC6/TTCTGAGCCACTTGGACTGAG<u>CCCTCTCTTTTTCTTACT</u>TTCT |

Microarray printing

The chips used for the printing were CodeLink Activated Slides (Amersham Biosciences) that covalently immobilize amine-modified DNA. The printing mix was: 20 µM amine-modified first probe DNA, 60 µM DNA spacer (PolyT), and 1× printing buffer (50 mM sodium phosphate, pH 8.5). The printing was performed with an OmniGrid™ printer (GeneMachines™). Each probe sample was printed 4 or 5 times per array and 2 arrays were present in each chip. The slides were left overnight in a humid chamber and the day after were blocked with 0.1 M Tris, 50 mM ethanolamine at pH 9. Control oligonucleotides used to verify array quality (SEQ IDs: 8-10) included a poly-T (20 bp) with 5'-amine and internal-biotin modification as a labeling control (amino-P), a 5'-amine-modified oligonucleotide with internal-Cy3 (amino-B) as an internal control for each spot's quality, and a 5'-amino modified poly-T (20 bp) as a DNA spacer (Table 2).

TABLE 2

| Control | SEQ ID NO: | Sequence |
|---|---|---|
| Amino-P | 8 | 5'-AmMC6/poly T(20)/Biotin |
| Amino-B | 9 | 5'-AmMC6/TCTGAGCCACTTGGACTGAG/Cy3 |
| Spacer | 10 | 5'-AmMC6/poly T (20)/ |

Target Preparation

The first targets used were target oligonucleotides (oligos) having a known sequence; different STR loci and different numbers of repeats were tested. The target oligos had the unique sequence described in Table 1 at the 3' end, repeats and a universal sequence (non-genomic sequence, the same for all the STR loci) at the 5' end. To obtain these target oligos two PCR reactions were conducted on plasmids containing repeat regions, a unique sequence for each STR locus and a universal region. The first PCR reaction used unique and universal primers. The second PCR reaction used only biotinylated universal primer in order to obtain labeled single stranded DNA.

The second targets used were two STR regions that were PCR-amplified from 20 human subjects using commercially available genomic DNA samples (Serological Research Institute, www.serological.com) with known STR profiles. PCR primers F-D7 and R-D7 were used to amplify locus D7S820; primers F-D16 and R-D16 were used to amplify locus D16S539 (Table 3). These primers were designed to amplify the entire STR region plus flanking DNA (the reverse complement of the clamp sequence on the probe oligonucleotides). PCR to amplify the STR loci was carried out in three steps. First, we used the AmpFlSTR Profiler Plus™ PCR Amplification Kit, which amplifies 13 different STR loci, using the suggested protocol (~1 ng total genomic DNA in a 25 µl reaction volume). PCR was performed as follows: 95° C. for 15 minutes, 28 cycles of 95° C., 59° C., and 72° C. for 1 minute each, and a 60 minute final extension at 60° C. Second, 0.5 µl of this PCR product was used as template for a second round of PCR to target the two STR loci of interest (D7S820 or D16S539) using 0.2 µM of each primer (F-D7/R-D7 or F-D16/R-D16). The size of the PCR products was verified by agarose gel chromatography. Third, a biotinylated, single-stranded target was generated by re-amplifying the targets with biotinylated F-D7 or F-D16 primers. 1 µl of the previous PCR product was used as template with 0.4 pmol biotinylated F-D7 or F-D16primer, using Titanium Taq DNA Polymerase (BD Biosciences Clontech). PCR was performed as follows: 95° C. for 10 minutes, 30 cycles of 95° C., 55° C. and 72° C. for 30 seconds each, and a 5 minute final extension at 72° C.

TABLE 3

| Primer | SEQ ID NO: | Sequence |
|---|---|---|
| B-F-D7 | 11 | 5'-Biotin/CTTGTCATAGTTTAGGAACGAACTAACGATA |
| R-D7 | 12 | 5'-TATTTAGTGAGATAAAAAAAACTATCAATCTGTC |
| B-F-D16 | 13 | 5'-Biotin/GATCAATACAGACAGACAGACAGGTGGATA |
| R-D16 | 14 | 5'-TATCTATCATCCATCTCTTGTTTTGTCTTTCAATGA |

First Hybridization

For the synthetic oligos, after PCR purification with QIAquick PCR Purification Kit (Qiagen), hybridization was performed overnight at 50° C. in the presence of 30 µl PCR product, 2× hybridization buffer (100 mM MES, 1M [Na+], 20 mM EDTA, 0.01% Tween20), 1.25×Denhardt's solution and 1 µl of a fluorescently labeled universal oligo with phycoerythrin (which was complementary to the common sequence present in all of the printed oligos). For human STRs, hybridization was performed at 42° C. for 12-16 hours in the presence of 50 µl of single-stranded target.

Second/Third Hybridization

In one embodiment, after washing the chip twice in SSPE 6× and Tween 0.1% at 50° C. for 1 min and once in SSPE 6× and Tween 0.1% at room temperature for 1 min, a second hybridization (branch migration) was conducted with one of the amino-oligos used for the printing that had a higher number of repeats than the target oligo. This hybridization was conducted with 7.5 pmol/μl of oligo (250 times more concentrated than what was used in the printing mix), 10 mM $MgCl_2$ and 4 ×SSC for 4 hours at 50° C. The chips were then washed twice in SSPE 6× and Tween 0.1% at 50° C. for 1 min and once in SSPE 6× and Tween 0.1% at room temperature for 1 min. Next, the chip was labeled with 0.0017 μg/μl streptavidin-allophycocyanin conjugate, 6×SSPE, 1×Denhardt's solution and 0.01% Tween 20 for 10 min at 50° C. The chip was then washed twice in SSPE 6× and Tween 0.1% at 50° C. for 1 min and once in SSPE 6× and Tween 0.1% at room temperature for 1 min.

In an alternative embodiment, after hybridization, the microarray was washed with wash buffer (6×SSPE, 0.1% Tween-20) twice for 2 minutes at 50° C. and once for 2 minutes at room temperature. The second hybridization was then performed using a competing mixture (5 μl $MgCl_2$ (1M) and 60 μL of 4×SSC) containing 10 μl of competing probe1 (D7-Comp1 or D16-Comp1, 100 μM final concentration, Table 1). This hybridization was carried out for 2 hours at 50° C. Following this hybridization, the slide was washed 3 times in wash buffer. Next, a third hybridization was performed using 10 μl of competing probe2(D7-Comp2 or D16-Comp2, 100 μM final concentration, Table 1) in the mixture. After the final hybridization, the microarray was washed 3 times in wash buffer and labeled for 10 min at 50° C. with a solution containing streptavidin-allophycocyanin (1 mg/ml final concentration), 6×SSPE, 1×Denhardt's solution, and 0.01% Tween-20.

For both embodiments, after the final hybridization, the microarray was scanned for fluorescent intensity at 535 and 635 nm using a GenePix 4000 fluorescent scanner (Axon Instrument, Foster City, Calif.) set to scan at 450 PMT. GenePix Pro software was used to determine the total fluorescent signal from each spot on the array.

Development of ANN Software to Analyze Primary Array Data

We used artificial neural network (ANN) software to recognize patterns of fluorescence peak amplitudes characteristic for specific numbers of repeats in our STR microarray analysis. The neural network training process was performed with a back-propagation neural network, BrainMaker Professional 3.52 (California Scientific Software, Berkeley), which includes elaborate training tools to optimize number of neurons, hidden layers, and training/testing parameters. Our STR-optimized network used 18 neurons in the first hidden layer and 13 neurons in the second hidden layer. The number of input neurons, 22, is equal to the number of repeats in the longest probe on the array. Two neurons were used in the output layer, which correspond to the heterozygous and homozygous classifications. The neural network training set consisted of 65 STR microarray runs (1 run represents 1 slide with 22 probe spots) with at least two replicates per sample. We then tested the neural network on seven test samples of known STR repeat length (~10% of total samples) with peaks in the repeat range of trained samples. The results showed that this trained neural network evaluated test samples with a 100% success rate and with a likelihood score of at least 90%, indicating that our ANN is sufficient for robust pattern recognition of STR samples.

Results

Results from Two-Hybridization Embodiment

FIG. 3 shows images of a chip before hybridization (FIG. 3A), after the first hybridization (FIGS. 3B and C) and after the second hybridization, i.e. branch migration (FIG. 3D). In FIG. 3A, the green spots show where the first probes were printed, in this case probes that detect STR DS18S51 with from 1 to 16 repeats (labeled as D18-1 to D18-16). There were four first probes printed for each STR repeat number, shown by the four green spots corresponding to each labeled first probe. In FIG. 3B, the red spots demonstrate binding of biotinylated target (red) to an unlabeled probe. In FIG. 3C, the yellow spots show where there are both first labeled probes printed (green) and biotinylated target (red) hybridized to the first probes. As can be seen from FIG. 3C, the first hybridization conditions successfully allow target to hybridize to all the first probes. FIG. 3D shows an image of a chip that was first hybridized with a biotinylated target oligo containing 3 repeats, and was then hybridized with a second probe containing 5 repeats. The image shows that the target oligo was displaced from the eight spots corresponding to first probes having 1 and 2 repeats (i.e. there is only green label on these spots, corresponding to the presence of first probes). In contrast, the target oligo remained hybridized to the spots corresponding to first probes having from 3 to 16 repeats (i.e. there is yellow label on these spots, corresponding to the presence of both first probe and biotinylated target). Thus, the number of repeats in the target oligo can be determined to be 3.

Results from Three-Hybridization Embodiment

To demonstrate the feasibility of three-hybridization embodiment, we tested our assay by generating a microarray with probes of all possible lengths for two human STR loci, D7 and D16. We then applied 20 commercially available human DNA samples to the array, carried out the procedure, and determined the STR profile to determine whether the predicted profile matched the known STR profile for these DNAs.

We designed probe oligonucleotides (Table 1) that contained (from 5' to 3'), the chemistry necessary for coupling to the microarray, a clamp sequence that flanks the human STRs of interest, and from 1 to 22 repeats of a 4-mer corresponding to human STR loci D7 or D16. All probes were spotted as individual features on an array as described above.

Using PCR, we generated target DNA with a known STR profile from commercially available DNAs. These targets were PCR-amplified using an oligonucleotide containing a clamp DNA sequence and a 5' biotin label (Table 3). These "test" targets were hybridized to the microarray by conventional means. The array was subsequently treated with two additional rounds of hybridization using synthetic oligonucleotides with 22 STR repeats (Table 1). This removed the biotin tagged targets from spots with probes that were unequal to a given STR length. Finally, the array was treated with a streptavidin-coupled fluorophore, which binds to the biotin label, and fluorescence on the array was quantified.

Figure 4:
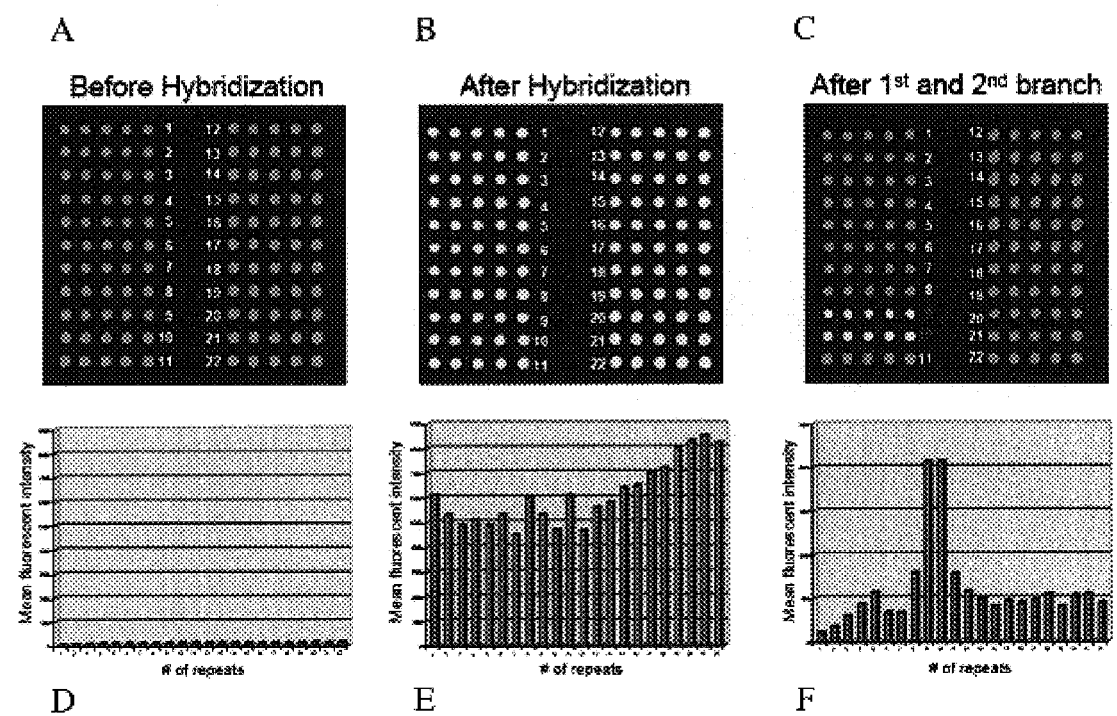
FIG. 4 shows an example of results from the embodiment of the branch migration assay shown in FIG. 2.

In control experiments in which an internal control oligonucleotide was hybridized to the array, the fluorescence intensity was similar on all probe spots (FIG. 4A). The green spots show where the first probes were printed. When test target DNA was hybridized to the array without the subsequent two additional rounds of hybridization, the fluorescence on all 22 probe spots was similar in intensity (FIG. 4B). However, after the two additional subsequent hybridization steps were carried out, the fluorescent signal from the features where the probe and test target differed in length were significantly weaker than the signal from the features where the two lengths were similar (FIG. 4C). Thus, the number of repeats in the target could be inferred from the known identities of the probes attached to the features with highest fluorescent signal. FIGS. 4D, E, and F depict the quantified fluorescence intensity of each probe spot of FIG. 4S A, B, and, C, respectively.

Example of Sample Analysis According to the Present Invention

Figure 5:
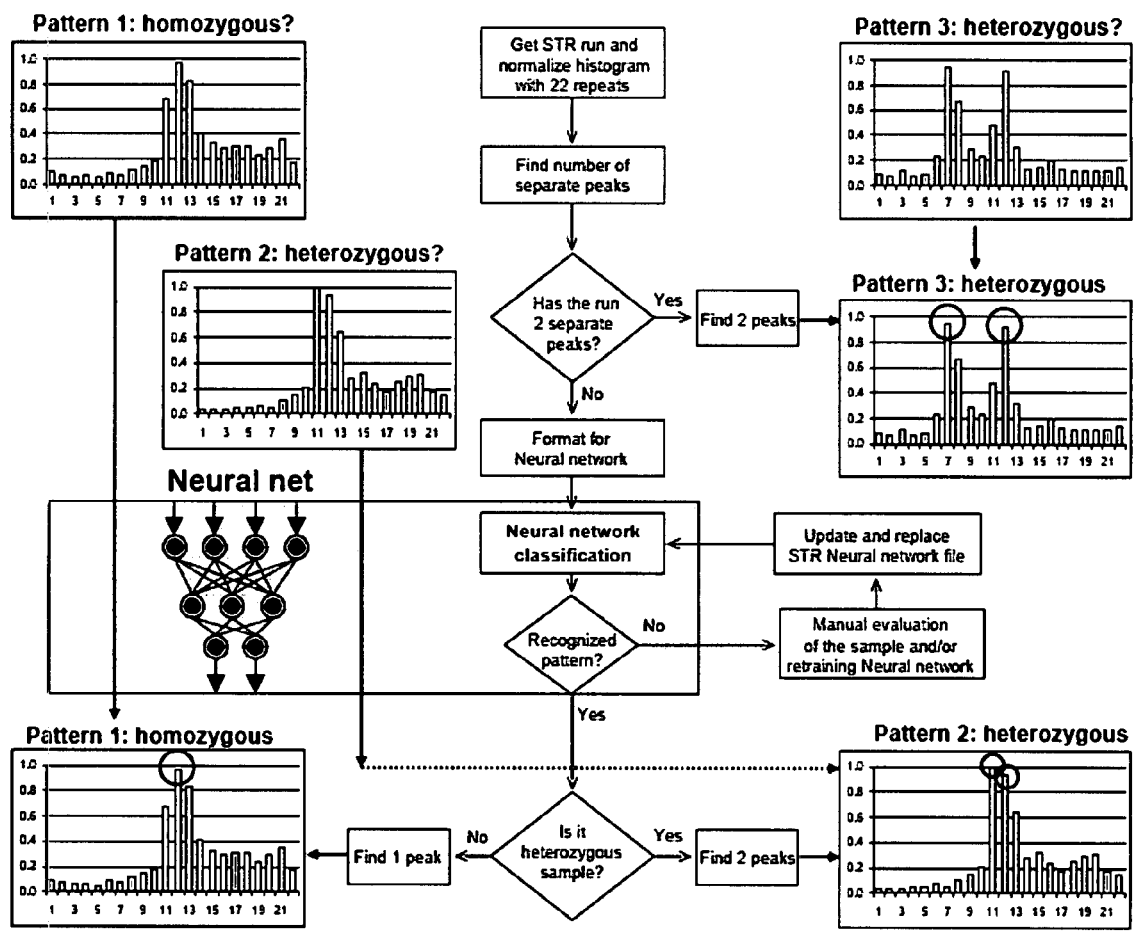
FIG. 5 shows an example of a neural network for determining whether a target came from a homozygous or a heterozygous sample according to the present invention.

FIG. 5 shows an example of a flow diagram of sample analysis by ANN. Pattern 1(homozygous) and pattern 2 (heterozygous) samples represent cases with fluorescence intensities that are somewhat similar; therefore ANN is used for identifying type of the sample. Pattern 3 (heterozygote with clearly identifiable fluorescent peaks) can be identified by a simple mathematical algorithm, but can also be identified by ANN.

Although the present invention and its advantages have been described in detail, it should be understood that the present invention is not limited by what is shown or described herein. As one of ordinary skill in the art will appreciate, the DNA fingerprinting methods disclosed herein could vary or be otherwise modified without departing from the principles of the present invention. Accordingly, the scope of the present invention should be determined by the following claims and their legal equivalents.

What is claimed is:

1. A method of determining the length of a polynucleotide target, comprising:
   (a) hybridizing said polynucleotide target to an array of first probes having different, determined lengths to form duplexes between said polynucleotide target and said first probes;
   (b) hybridizing a second probe having a determined length to said duplexes, wherein said second probe displaces said polynucleotide target from said duplex if the length of said polynucleotide target is greater than the length of said first probe;
   (c) hybridizing a third probe having a determined length to said duplexes, wherein said third probe displaces said polynucleotide target from said duplex if the length of said polynucleotide target is less than the length of said first probe;
   (d) determining the length of said polynucleotide target by identifying in which of said duplexes said polynucleotide target was not displaced.

2. The method as set forth in claim 1, wherein said polynucleotide target, said first probes, and said second probe comprise single-stranded DNA, double-stranded DNA, or nucleic acid analogs.

3. The method as set forth in claim 1, wherein said polynucleotide target, said first probes, and said second probe comprise repeated nucleotide sequences, and wherein the length of said polynucleotide target, said first probes, and said second probes is determined by the number of said repeated nucleotide sequences.

4. The method as set forth in claim 3, wherein said repeated nucleotide sequences comprise two to seven base pairs.

5. The method as set forth in claim 3, wherein said first probes said second probe, and said third probe further comprise a non-repeated nucleotide sequence that is complimentary to a non-repeated nucleotide sequence in said target.

6. The method as set forth in claim 3, wherein said determining further comprises determining the number of said repeated nucleotide sequences in said polynucleotide target.

7. The method as set forth in claim 1, wherein said second probe has a nucleotide or nucleotide analog sequence that is identical to the nucleotide or nucleotide analog sequence of one of said first probes.

8. The method as set forth in claim 1, wherein said third probe has a nucleotide or nucleotide analog sequence that is complementary to the nucleotide or nucleotide analog sequence of one of said first probes.

9. The method as set forth in claim 1, further comprising labeling said polynucleotide target.

10. The method as set forth in claim 9, wherein said label comprises biotin, fluorescent particles, or magnetic nanoparticles.

11. The method as set forth in claim 1, further comprising attaching said array of first probes to a solid support.

12. The method as set forth in claim 11, wherein said first probes are attached to predetermined positions on said solid support.

13. The method as set forth in claim 1, wherein said second probe and said third probe have a length equal to the longest of said first probes.

14. The method as set forth in claim 1, wherein said determining further comprises assessing whether said polynucleotide target is from a homozygous or a heterozygous sample.

15. The method as set forth in claim 14, wherein said assessing utilizes software based on a multilayer artificial neural network.

* * * * *